United States Patent [19]

Mita et al.

[11] Patent Number: 5,461,158
[45] Date of Patent: Oct. 24, 1995

[54] SUBSTITUTED BUTANEOLIDES AND BUTANE LACTAMS, AND PHARMACEUTICAL USE THEREOF

[75] Inventors: Shiro Mita, Ashiya; Yoichi Kawashima, Kyoto; Katsuhiko Nakata, Sakurai, all of Japan

[73] Assignee: Santen Pharmaceutical Co., Ltd., Osaka, Japan

[21] Appl. No.: 81,340

[22] PCT Filed: Jan. 7, 1992

[86] PCT No.: PCT/JP92/00002

§ 371 Date: Jun. 2, 1994

§ 102(e) Date: Jun. 2, 1994

[87] PCT Pub. No.: WO92/12129

PCT Pub. Date: Jul. 23, 1992

[30] Foreign Application Priority Data

Jan. 10, 1991 [JP] Japan ..................... 3-069583

[51] Int. Cl.⁶ ............... C07D 301/28; C07D 207/18; A61K 31/365; A61K 31/40
[52] U.S. Cl. ............... 548/551; 549/453; 514/428; 514/461
[58] Field of Search ............... 548/551; 549/453; 514/428, 461

[56] References Cited

U.S. PATENT DOCUMENTS

| | | | |
|---|---|---|---|
| 4,613,613 | 9/1986 | Oguri et al. | 514/44 |
| 5,292,767 | 3/1994 | Mita et al. | 514/444 |
| 5,350,860 | 9/1994 | Mita et al. | 514/453 |

FOREIGN PATENT DOCUMENTS

| | | |
|---|---|---|
| 41-6331 | 4/1966 | Japan. |
| 56-104864 | 8/1981 | Japan. |

OTHER PUBLICATIONS

Bach et al., "Thymulin, A Zinc–Dependent Hormone", vol. 6, No. 1, pp. 25–29, 1989, Med. Oncol. & Tumor Pharmacother.

*Primary Examiner*—David B. Springer
*Attorney, Agent, or Firm*—Frishauf, Holtz, Goodman, Langer & Chick

[57] ABSTRACT

This invention offers novel compounds of the formula [I] which are useful for treatment of various immune diseases such as immunodeficiency and autoimmune diseases caused by immuno disorders, and synthetic intermediates thereof represented by the formula [II],

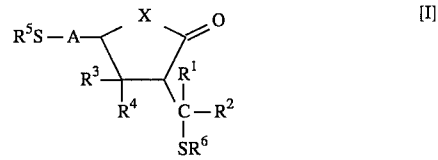

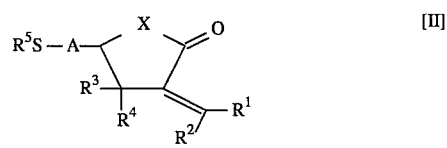

wherein X is oxygen or $NR^7$ and the $R_1$–$R_7$ groups are defined in the specification.

17 Claims, No Drawings

SUBSTITUTED BUTANEOLIDES AND BUTANE LACTAMS, AND PHARMACEUTICAL USE THEREOF

FIELD OF THE INVENTION

This invention offers novel compounds which are useful for treatment of diseases such as immunodeficiency and autoimmune diseases caused by various immune disorders, and synthetic intermediates therefor.

BACKGROUND ART

Recently, many studies have been performed on mechanisms and therapeutic agents for diseases caused by various immune disorders or immune depression caused by adverse reactions of carcinostatic drugs. It is known that thymulin, a nonapeptide produced in the thymus, forms a complex with zinc and improves a depressed immunity. It is suggested that it could be an effective drug on immunodeficiency and autoimmune diseases (Med. Oncol. & Tumor Pharmacother. 6, 25–29, 1989).

However, there remain many problems in the practical use of thymulin. For example, the availability of thymulin is limited due to a small yield in the thymus and duration of the activity thereof is short because thymulin is easily decomposed by endogenous enzymes.

Therefore, synthetic compounds are desired which have a long lasting activity and can be prepared in a large amount. But few studies have been performed on such synthetic compounds having thymulin-like activities.

The inventors focused on the action mechanisms of thymulin forming a complex with zinc and studied to synthesize various novel compounds having sulfur atoms in the side chains.

The inventors also examined the effect of the obtained novel compounds. As the result of the precise studies, the inventors found that lactone or lactam compounds having sulfur atoms in the side chains showed excellent thymulin-like activities. Although many studies have been performed on lactone or lactam compounds, few compounds having sulfur atoms in the side chains were known. As mentioned later, the structural characteristic of the compounds of this invention of the formula [I] is that two intramolecular sulfur atoms exist in the side chains of lactone or lactam compounds. Such lactone or lactam compounds have not been reported.

DESCRIPTION OF THE INVENTION

This invention relates to a compound of the formula [I] and salts thereof; and a synthetic intermediate represented by the formula [II] and salts thereof,

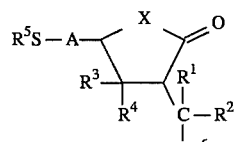
[I]

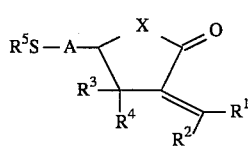
[II]

wherein $R^1$ and $R^2$ are the same or different and each is hydrogen or lower alkyl;

$R^3$ and $R^4$ are the same or different and each is hydrogen, lower alkyl, carboxy or lower alkoxycarbonyl;

$R^5$ and $R^6$ are the same or different and each is hydrogen, lower alkyl, lower alkenyl, lower alkanoyl, phenyl lower alkyl, phenylcarbonyl, trityl or tetrahydropyranyl, and the phenyl ring of the said phenyl lower alkyl or phenylcarbonyl can be substituted by lower alkyl, lower alkoxy, halogen, carboxy or lower alkoxycarbonyl;

X is oxygen or $NR^7$;

$R^7$ is hydrogen, lower alkyl, lower alkoxy, phenyl lower alkyl or phenyl lower alkoxy, and said alkyl group can be substituted by carboxy, lower alkoxycarbonyl, amino, lower alkylamino, lower alkoxycarbonylamino or phenyl lower alkylamino, and the phenyl ring of the said phenyl lower alkyl, phenyl lower alkoxy or phenyl lower alkylamino can be substituted by lower alkyl, lower alkoxy, halogen, carboxy or lower alkoxycarbonyl, and A is straight or branched lower alkylene.

The same shall be applied hereinafter.

The groups defined above are explained as follows in more detail.

The term "lower alkyl" intends to designate straight or branched alkyl having 1 to 6 carbon atoms exemplified by methyl, ethyl, propyl, hexyl, iso-propyl and t-butyl.

The term "lower alkenyl" intends to designate straight or branched alkenyl having 2 to 6 carbon atoms containing double bond exemplified by vinyl, allyl and hexenyl.

The term "lower alkanoyl" intends to designate straight or branched alkanoyl having 2 to 6 carbon atoms exemplified by acetyl, propionyl, hexanoyl, iso-propionyl and pivaloyl. The term "lower alkoxy" intends to designate straight or branched alkoxy having 1 to 6 carbon atoms exemplified by methoxy, ethoxy, propoxy, hexyloxy, iso-propoxy and t-butoxy. The term "lower alkylene" intends to designate straight or branched alkylene having 1 to 6 carbon atoms exemplified by methylene, ethylene, trimethylene, tetramethylene, hexamethylene, (dimethyl)methylene and (diethyl) methylene. The term "halogen" intends to designate fluorine, chlorine, bromine and iodine.

Examples of the salts are sodium salt, potassium salt, calcium salt, magnesium salt, zinc salt, hydrochloric acid salt, sulfuric acid salt, phosphoric acid salt, lactic acid salt, maleic acid salt, fumaric acid salt and oxalic acid salt, which are pharmaceutically acceptable salts.

The typical synthetic method of the compounds of the formula [I] is shown below. This reaction is an addition reaction of a compound of the formula [II] to a thiol compound of the formula [III].

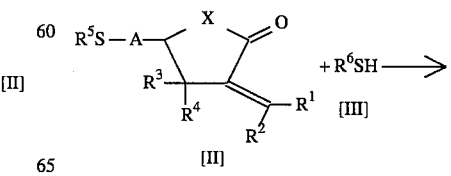

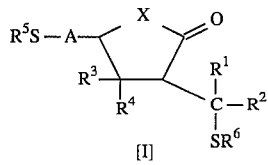

The reaction conditions generally used in an addition reaction of a thiol compound to a compound having a double bond can be applied to the above reaction, and the conditions should not be restricted. But preferably a catalyst such as n-butyllithium can be used to perform the reaction smoothly.

The compound of the formula [I] wherein X is oxygen, namely a lactone compound, can be also prepared by a cyclization reaction of the compound of the formula [IV],

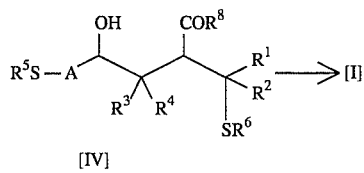

wherein $R^8$ is amino or lower alkoxy. The same shall be applied hereinafter.

In the above reactions, when $R^5$ or $R^6$ plays a role of a protective group of SH group, such protective group can be removed by the usual method in a desirable reaction step. In the reverse order, a group defined in $R^5$ or $R^6$ except hydrogen can be introduced after obtaining a thiol compound.

When X is $NR^7$ and $R^7$ plays a role of a protective group of NH group, the protective group can be removed by the usual method in a desirable reaction step.

When $R^7$ further contains a protected amino group, the protective group can be also removed by the usual method in a desirable reaction step.

When an ester group is contained in an obtained compound, the ester group can be hydrolyzed by the usual method to convert into a carboxylic acid derivative.

The typical synthetic routes of the compounds of the formula [II], synthetic intermediates, are shown below.

1) lactone compound a)

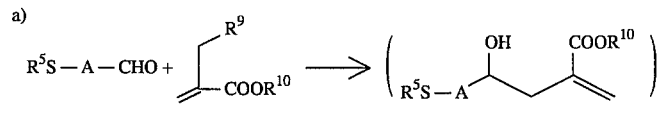

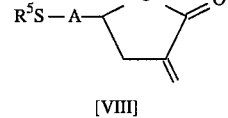

b)

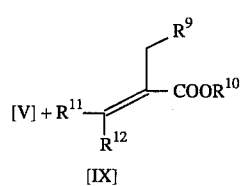

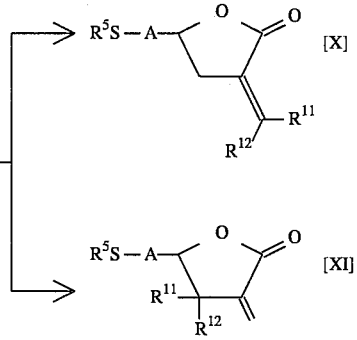

c)

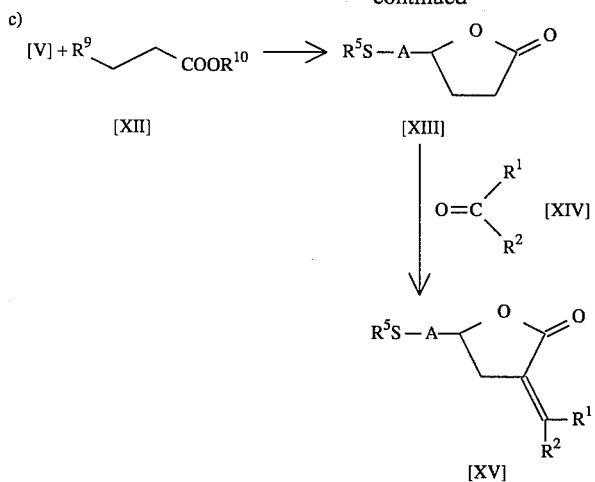

d)

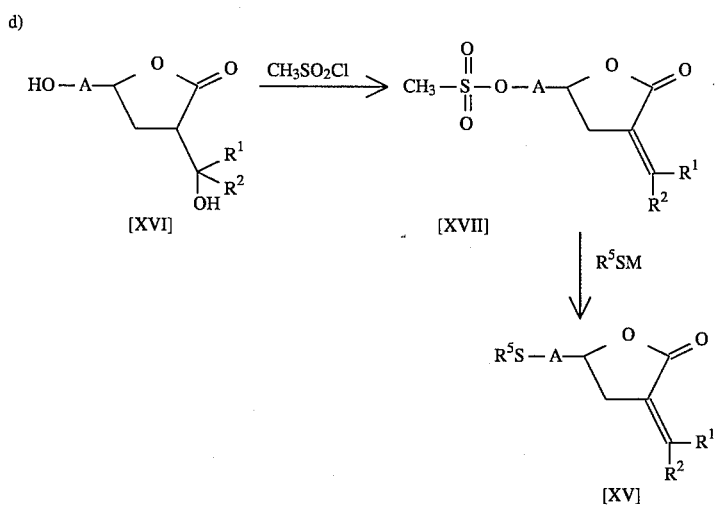

In the above reaction schemes, $R^9$ is halogen, $R^{10}$ is lower alkyl, $R^{11}$ or $R^{12}$ corresponds to the pair of $R^1$ and $R^2$ or $R^3$ and $R^4$, respectively. The same shall be applied hereinafter.

In the above reaction, the compound of the formula [VII] can be either isolated or not isolated.

The compound of the formula [I] can be obtained by reacting the compound of the formula [VII] with a thiol compound of the formula [III] directly, not by inducing the compound of the formula [VIII] from the compound of the formula [VII].

2) lactam compound a)
$$R^5S-A-CHO + NH_2-R^7 \longrightarrow R^5S-A-CH=N-R^7$$
$$[V] \qquad\qquad [XVIII] \qquad\qquad\qquad [XIX]$$

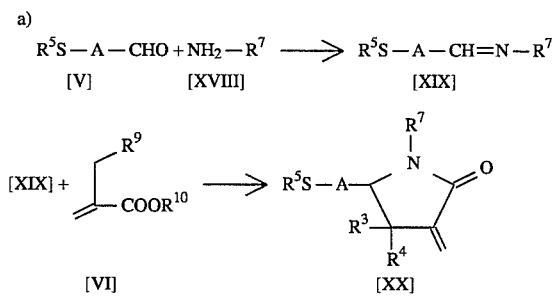

-continued
b)
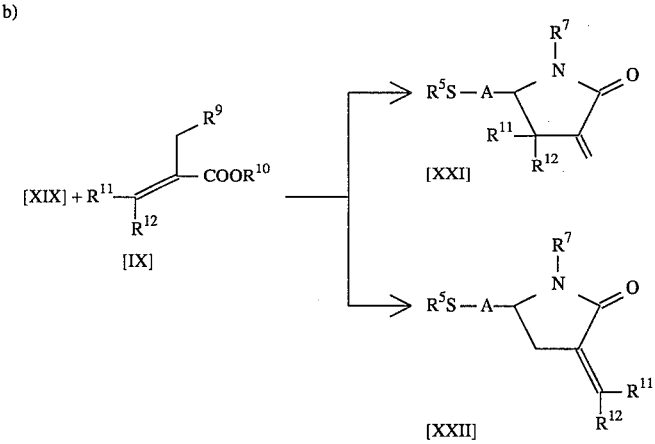
c)
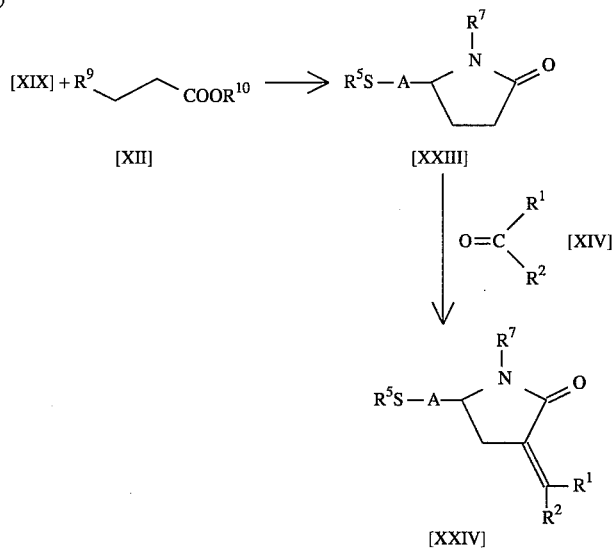
d)
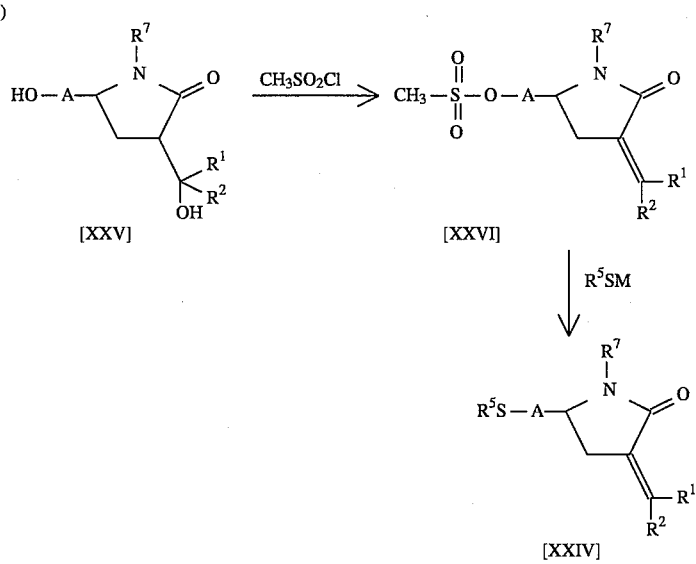
The compound of the formula [XIX] should be isolated to be applied to a next reaction step if possible. But, if the isolation is not easy, the compound can be applied to a next reaction step without an isolation procedure.
The compounds prepared by the above reaction methods can be converted into the salts as mentioned before by the usual method.

The compounds of the formula [I] and [II] have optical isomers or stereoisomers, and these isomers are included in this invention.

The nomenclature of the compound of this invention is given as follows.

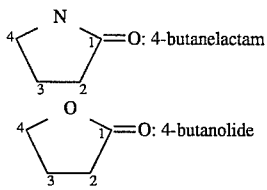

In the following nomenclature of the compounds, cis or trans means that the conformation of the groups substituted in the 2- and 4-position is cis or trans. When such indication is not given, a compound is a mixture of cis-form and trans-form or the conformation of cis or trans is not identified yet.

The compound of the formula [I] of this invention has excellent thymulin-like activities and is expected to be useful for treatment of various diseases, which are caused by immune disorders, such as immunodeficiency and autoimmune diseases. It is known that thymulin, a nonapeptide produced in the thymus, forms a complex with zinc and improves a depressed immunity. It is also suggested that thymulin has a possibility to be useful for immunodeficiency or autoimmune diseases.

However, there remain many problems in the practical use of thymulin. Therefore, the inventors focused on the action mechanism of thymulin and synthesized various novel compounds to examine the thymulin-like activities.

As the result of the precise studies, the inventors found that lactone or lactam compounds having intramolecular sulfur atoms in the side chains had excellent thymulin-like activities as shown in the article of pharmacological test and were useful for treatment of diseases, which were caused by various immune disorders, such as immunodeficiency and autoimmune diseases.

There are various immune disorders, for example, rheumatoid arthritis, chronic hepatitis, anemia, systemic lupus erythematosus, primary immunodeficiency and hypo-γ-globulinemia. The compound of this invention of the formula [I] is expected to be useful for treatment of such diseases.

It is presumed that the compound of this invention forms a complex with zinc and acts practically like thymulin.

In practical use, the complex can be formed by taking zinc which exist in vivo in a small amount. Zinc can be also supplied by an administration of zinc salt such as zinc chloride together with the compound of this invention.

The compound of this invention of the formula [I] can be administered orally or parenterally. As the dosage forms, tablet, capsule, soft capsule, injection, etc., can be used. The preparations can be prepared by the usual method. For example, oral preparations such as a tablet, capsule, soft capsule and granule can be produced by adding as diluent such as lactose, starch, crystalline cellulose or vegetable oil; a lubricant such as magnesium stearate or talc; a binder such as hydroxypropylcellulose or polyvinylpyrrolidone; a disintegrator such as carboxymethylcellulose calcium; a coating agent such as hydroxypropylmethylcellulose, macrogol or silicone resin; and a coating film such as gelatin, if necessary.

The dosage of the compound of this invention can be adjusted depending on symptom, dosage form, etc. The usual daily dosage is 1–1000 mg, preferably 1–200 mg, which can be given in one or a few divided doses.

EXAMPLE

Reference Example 1

5-benzylthio-4-hydroxy-5-methyl-2-methylenehexanoic acid methyl ester

To a stirred suspension of chromic chloride (5.00 g) in THF (50 ml), 2-benzylthio-2-methylpropionaldehyde (3.00 g) and methyl 2-bromomethylacryrate (1.86 ml) dissolved in tetrahydrofurane (THF, 50 ml) were added dropwise under nitrogen atmosphere and ice-cooling. After the addition, the mixture was stirred for 30 minutes under ice-cooling and for 4 hours at room temperature. To the mixture saturated aqueous ammonium chloride solution (100 ml) was added and extracted with ether. The organic layer was washed with saturated sodium chloride solution, dried over anhydrous sodium sulfate and concentrated in vacuo. The oily residue was purified by a silica gel column chromatography to give 3.60 g (79%) of the titled compound.

IR (film, cm$^{-1}$) 3440, 1718, 1628, 1437, 1200, 1144, 709.

Reference Example 2

N-[2-(4-methoxybenzylthio)-2-methylpropylidene] benzylamine

To a stirred solution of 2-(4-methoxybenzylthio)-2-methylpropionaldehyde (6.00 g) in benzene (60 ml), molecular sieve (4A, 5 g) and benzylamine (3.15 g) were added at room temperature.

The mixture was stirred for 5 hours at room temperature and filtered. The filtrate was concentrated in vacuo to give 8.38 g (quantitative yield) of the titled compound.

IR (film, cm$^{-1}$) 2960, 2924, 2836, 1653, 1611, 1513, 1453, 1301, 1249, 1175, 1034, 733, 699.

By substituting starting materials, the following compounds can be prepared by the similar method as Reference Example 2.

N-(2-benzylthio-2-methylpropylidene) benzylamine
  IR (film, cm$^{-1}$) 1654, 1602, 1494, 1452, 1363, 1028, 697.
N-(2-benzylthio-2-methylpropylidene)-4-methoxycarbonyl-benzylamine
  IR (film, cm$^{-1}$) 2964, 1721, 1655, 1435, 1279, 1107, 756, 708.
benzylthioacetaldehyde oxime O-benzyl ether
  IR (film, cm$^{-1}$) 3029, 2920, 1495, 1453, 1415, 1366, 1311, 1209, 1070, 1013, 916, 736, 698.
benzylthioacetaldehyde oxime O-methyl ether
  IR (film, cm$^{-1}$) 3028, 2937, 2817, 1494, 1453, 1414, 1088, 1071, 1030, 915, 770, 700.
N-(2-benzylthio-2-methylpropylidene)ethoxycarbonylmethylamine
  IR (film, cm$^{-1}$) 2974, 1745, 1659, 1495, 1454, 1367, 1338, 1189, 1127, 1061, 1030, 713.
N-(2-benzylthio-2-methylpropylidene)-5-(tert-butoxycarbonylamino) pentylamine
  IR (film, cm$^{-1}$) 3357, 2970, 2930, 2859, 1713, 1657, 1514, 1454, 1365, 1249, 1172, 712.

Example 1

4-(1-benzylthio-1-methylethyl)-2-methylene-4-butanolide (compound No. 1-1)

To a solution of 2-benzylthio-2-methylpropionaldehyde (3.26 g) in THF (80 ml), zinc dust (2.56 g) activated with hydrochloric acid and a small amount of iodine were added. To the mixture methyl 2-bromoacrylate (3.00 g) dissolved in THF (20 ml) was added dropwise. The mixture was stirred for 3 hours under ultrasonic irradiation and filtrated by celite. To the filtrate ether was added. The organic layer was washed with water and saturated sodium chloride solution, dried over anhydrous sodium sulfate and concentrated in vacuo. The oily residue was purified by silica gel column chromatography to give 4.31 g (97%) of the titled compound.

IR (film, cm$^{-1}$) 1761, 1454, 1333, 1280, 1256, 1122, 998, 985, 711.

By substituting starting materials, the following compounds can be prepared by the similar method as Example 1.

4-(4-methoxybenzylthiomethyl)-2-methylene-4-butanolide (compound No.1-2)

IR (film, cm$^{-1}$) 3000, 2928, 2836, 1766, 1610, 1514, 1464, 1440, 1301, 1242, 1120, 1031, 834, 812.

4-(1-tritylthio-1-methylethyl)-2-methylene-4-butanolide (compound No.1-3)

IR (film, cm$^{-1}$) 3057, 3019, 1766, 1444, 1280, 1120, 755, 701.

4-benzylthiomethyl-2-methylene-4-butanolide (compound No.1-4)

IR (film, cm$^{-1}$) 3028, 2920, 1770, 1664, 1601, 1494, 1454, 1337, 1121, 1014, 703.

4-tert-butylthiomethyl-2-methylene-4-butanolide (compound No.1-5)

IR (film, cm$^{-1}$) 2961, 1763, 1365, 1278, 1159, 1120, 1010.

4-(1-tert-butylcarbonylthio-1-methylethyl)-2-methylene-4-butanolide (compound No. 1-6)

IR (film, cm$^{-1}$) 2971, 1771, 1724, 1676, 1123, 936, 810.

4-(2-benzylthioethyl)-2-methylene-4-butanolide (compound No.1-7)

4-(3-benzylthiopropyl)-2-methylene-4-butanolide (compound No.1- 8)

4-(4-benzylthiobutyl)-2-methylene-4-butanolide (compound No. 1-9)

4-(1-methyl-2-benzylthioethyl)-2-methylene-4-butanolide (compound No. 1-10)

4-(1-ethyl-1-benzylthiopropyl)-2-methylene-4-butanolide (compound No. 1-11)

4-methylthiomethyl-2-methylene-4-butanolide (compound No.1-12)

4-allylthiomethyl-2-methylene-4-butanolide (compound No.1-13)

4-(4-methylbenzylthiomethyl)-2-methylene-4-butanolide (compound No.1-14)

Example 2

4-(1-benzylthio-1-methylethyl)-3-methoxycarbonyl-2-methylene-4-butanolide (compound No. 2-1)

To a stirred suspension of zinc dust (0.67 g) activated with hydrochloric acid in THF (15 ml), 2-benzylthio-2-methylpropionaldehyde (1.00 g) dissolved in THF (5 ml) and dimethyl 2-bromomethylfumarate (1.28 g) dissolved in THF (5 ml) were added dropwise in the order named while refluxing under nitrogen atmosphere. The mixture was refluxed for an additional 1.5 hours and saturated aqueous ammonium chloride solution was added to it. After cooling the mixture was filtered by celite. A reaction product was extracted with ethyl acetate from the filtrate. The organic layer was washed with 1N hydrochloric acid, water and then saturated sodium chloride solution. The organic layer was dried over anhydrous magnesium sulfate and concentrated in vacuo. The oily residue was purified by silica gel column chromatography to give 0.63 g (38%) of the titled compound.

IR (film, cm$^{-1}$) 2970, 1769, 1731, 1668, 1496, 1437, 1386, 1340, 1230, 1144, 1094, 1026, 1002.

Example 3

4-(1-benzylthio-1-methylethyl)-2-ethylidene-4-butanolide (compound No.3-1) and

4-(1-benzylthio-1-methylethyl)-3-methyl-2-methylene-4-butanolide (compound No.3-2)

To a stirred suspension of zinc dust (0.77 g) activated with hydrochloric acid in THF (20 ml), 2-benzylthio-2-methylpropionaldehyde (2.00 g) dissolved in THF (10 ml) and methyl 2-bromomethylcrotonate (2.19 g) dissolved in THF (10 ml) were added dropwise in the order named at about 30° C. under nitrogen atmosphere and ultrasonic irradiation. The mixture was stirred over night at room temperature. Saturated aqueous ammonium chloride solution was added to the mixture and the mixture was filtered by celite. A reaction product was extracted with ethyl acetate from the filtrate. The organic layer was washed with 1N hydrochloric acid, water and then saturated sodium chloride solution. The organic layer was dried over anhydrous magnesium sulfate and concentrated in vacuo. The oily residue was purified and separated by silica gel column chromatography to give the each titled compound.

Example 4

4-acetylthiomethyl-2-isopropylidene-4-butanolide (compound No. 4-1)

1) To a stirred solution of 2-(1-hydroxy-1-methylethyl)-4-hydroxymethyl- 4-butanolide (0.45 g) in methylene chloride (8 ml), triethylamine (1.43 g) dissolved in methylene chloride (1 ml) and methanesulfonyl chloride (1.01 g) dissolved in methylene chloride (1 ml) were added in the order named under ice-cooling. The mixture was stirred for 2 hours under ice-cooling and diluted with chloroform. The mixture was washed with water and saturated sodium chloride solution. The organic layer was dried over anhydrous sodium sulfate and concentrated in vacuo. The oily residue was purified by silica gel column chromatography to give 0.36 g (60%) of the following compound.

2-isopropylidene-4-methanesulfonyloxymethyl-4-butanolide mp 50.9°–54.8° C. (ethyl acetate—n-hexane)

IR (KBr, cm$^{-1}$) 1740, 1665, 1349, 1173, 983, 956, 938, 822.

2) To a stirred solution of 2-isopropylidene-4-methanesulfonyloxymethyl- 4-butanolide (57 mg) and thioacetic acid (39 mg) in dry DMF (2 ml), potassium tert-butoxide (29 mg) was added under ice-cooling. The mixture was stirred overnight at room temperature and diluted with ethyl acetate. The mixture was washed with water and saturated sodium chloride solution. The organic layer was dried over anhydrous sodium sulfate and concentrated in vacuo. The oily residue was purified by silica gel column chromatography to give 25 mg (48%) of the titled compound (compound No.4-1).

IR (film, cm$^{-1}$) 1747, 1694, 1667, 1268, 1189, 1134, 1025.

Example 5

N-benzyl-4-[1-(4-methoxybenzylthio)-1-methylethyl]-2-methylene-4-butanelactam (compound No.5-1)

To a suspension of zinc dust (4.75 g) activated with hydrochloric acid in THF (75 ml), N-[2-(4-methoxybenzylthio)-2-methylpropylidene] benzylamine (7.60 g) and a small amount of iodine were added at 60° C. To the mixture methyl 2-bromoacrylate (4.77 g) dissolved in THF (25 ml) was added dropwise.

After the addition, the mixture was refluxed for 15 minutes and cooled to room temperature. The mixture was filtered by celite and the filtrate was concentrated in vacuo. The oily residue was dissolved in ethyl acetate, and the solution was washed with 1N hydrochloric acid, water and then saturated sodium chloride solution. The organic layer was dried over anhydrous sodium sulfate and concentrated in vacuo to give crystals. The crystals were collected by filtration to give 6.92 g (75%) of the titled compound.

mp 87.4°–88.5° C. (n-hexane—ethyl acetate).

IR (KBr, cm$^{-1}$) 2968, 2932, 1690, 1663, 1610, 1511, 1407, 1292, 1244, 1178, 1147, 1023, 913.

By substituting starting materials, the following compounds can be prepared by the similar method as Example 5.

N-benzyl-4-(1-benzylthio-1-methylethyl)-2-methylene-4-butanelactam (compound No.5-2)

IR (film, cm$^{-1}$) 3028, 2969, 2927, 1692, 1663, 1494, 1413, 1288, 1121, 921, 810, 703.

N-benzyl-4-benzylthiomethyl-2-methylene-4-butanelactam (compound No.5-3)

IR (film, cm$^{-1}$) 3028, 2917, 1689, 1660, 1494, 1417, 1294, 1242, 703.

N-benzyl-4-(2-benzylthio-2-methylpropyl)-2-methylene-4-butanelactam (compound No.5-4)

IR (film, cm$^{-1}$) 3018, 2932, 1680, 1660, 1442, 1426, 1367, 1316, 1288, 1221, 1213.

4-benzylthiomethyl-N-isopropyl-2-methylene-4-butanelactam (compound No.5-5)

IR (film, cm$^{-1}$) 2971, 2930, 1684, 1660, 1494, 1454, 1413, 1363, 1297, 1216, 920, 703.

4-(1-benzylthio-1-methylethyl)-N-ethoxycarbonylmethyl-2-methylene-4-butanelactam (compound No.5-6)

IR (film, cm$^{-1}$) 2977, 1745, 1698, 1664, 1495, 1425, 1290, 1199, 1026, 924, 810, 714.

4-(1-benzylthio-1-methylethyl)-N-(5-tert-butoxycarbonylaminopentyl)-2-methylene-4-butanelactam (compound No. 5-7)

IR (film, cm$^{-1}$) 3337, 2973, 2931, 2863, 1681, 1518, 1454, 1365, 1250, 1173, 919, 712.

N-(4-methoxycarbonylbenzyl)-4-(1-benzylthio-1-methylethyl)-2-methylene-4-butanelactam (compound No.5-8) mp 97.0°–102.1° C.

IR (KBr, cm$^{-1}$) 2959, 1714, 1684, 1656, 1281, 1111, 716.

N-benzyloxy-4-benzylthiomethyl-2-methylene-4-butanelactam (compound No.5-9) mp 74.1°–74.9° C. (isopropylether)

IR (KBr, cm$^{-1}$) 3030, 1701, 1658, 1492, 1454, 1397, 1290, 1020, 913, 762, 702.

4-benzylthiomethyl-N-methoxy-2-methylene-4-butanelactam (compound No.5-10)

IR (film, cm$^{-1}$) 2936, 1715, 1661, 1602, 1494, 1428, 1288, 1034, 947, 798, 770, 704.

N-benzyl-4-(3-benzylthiopropyl)-2-methylene-4-butanelactam (compound No. 5-11)

N-benzyl-4-(4-benzylthiobutyl)-2-methylene-4-butanelactam (compound No. 5-12)

N-benzyl-4-(2-benzylthio-1-methylethyl)-2-methylene-4-butanelactam (compound No.5-13)

N-benzyl-4-(1-benzylthio-1-ethylpropyl)-2-methylene-4-butanelactam (compound No.5-14)

N-benzyl-4-(1-methylthio-1-methylethyl)-2-methylene-4-butanelactam (compound No. 5-15)

4-(1-allylthio-1-methylethyl)-N-benzyl-2-methylene-4-butanelactam (compound No.5-16)

N-benzyl-4-[1-(4-methylbenzylthio)-1-methylethyl]-2-methylene-4-butanelactam (compound No.5-17)

N-(5-benzylaminopentyl)-4-(1-benzylthio-1-methylethyl)-2-methylene-4-butanelactam (compound No. 5-18)

4-(1-benzylthio-1-methylethyl)-N-(5-dimethylaminopentyl)-2-methylene-4-butanelactam (compound No.5-19)

N-(5-aminopentyl)-4-(1-benzylthio-1-methylethyl)-2-methylene-4-butanelactam (compound No. 5-20)

4-(1-benzylthio-1-methylethyl)-N-(4-methylbenzyl)-2-methylene-4-butanelactam (compound No.5-21)

4-(1-benzylthio-1-methylethyl)-N-(4-methoxybenzyl)-2-methylene-4-butanelactam (compound No.5-22)

4-(1-benzylthio-1-methylethyl)-N-(4-chlorobenzyl)-2-methylene-4-butanelactam (compound No.5-23)

4-(1-benzylthio-1-methylethyl)-N-(4-methylbenzyloxy)-2-methylene-4-butanelactam (compound No.5-24)

4-(1-benzylthio-1-methylethyl)-N-(4-methoxybenzyloxy)-2-methylene-4-butanelactam (compound No.5-25)

4-(1-benzylthio-1-methylethyl)-N-(4-chlorobenzyloxy)-2-methylene-4-butanelactam (compound No.5-26)

N-benzyl-2-methylene-(1-tritylthio-1-methylethyl)-4-butanelactam (compound No.5-27)

Example 6

N-benzyl-4-(1-benzylthio-1-methylethyl)-3-methoxycarbonyl-2-methylene-4-butanelactam (compound No.6-1)

To a stirred suspension of zinc dust (0.68 g) activated with hydrochloric acid in THF (15 ml), N-(2-benzylthio-2-methylpropylidene)benzylamine (1.42 g) dissolved in THF (15 ml) and dimethyl 2-bromomethylfumarate (1.28 g) dissolved in THF are added dropwise while refluxing under nitrogen atmosphere. The mixture is stirred for additional 1.5 hours under refluxing. To the mixture saturated aqueous ammonium chloride solution is added. After cooling, the mixture is filtered by celite. A reaction product is extracted with ethyl acetate from the filtrate. The organic layer is washed with 1N hydrochloric acid, water and then saturated sodium chloride solution. The organic layer is dried over anhydrous magnesium sulfate and concentrated in vacuo. The oily residue is purified by silica gel column chromatography to give the titled compound.

Example 7

N-benzyl-4-(1-benzylthio-1-methylethyl)-3-methyl-2-methylene-4-butanelactam (compound No.7-1) and N-benzyl-4-(1-benzylthio-1-methylethyl)-2-ethylidene-4-butanelactam (compound No.7-2)

To a stirred suspension of zinc dust (0.53 g) activated with hydrochloric acid in THF (20 ml), methyl 2-bromomethylcrotonate (1.50 g) dissolved in THF (10 ml) and N-(2-benzylthio-2-methylpropylidene)benzylamine (2.00 g) dissolved in THF (10 ml) were added dropwise in the order named at about 30° C. under nitrogen atmosphere and ultrasonic irradiation. The mixture was stirred overnight at room temperature. To the mixture saturated aqueous ammonium chloride solution was added. The mixture was filtered by celite. A reaction product was extracted with ethyl acetate from the filtrate. The organic layer was washed with 1N hydrochloric acid, water and then saturated sodium chloride solution. The organic layer was dried over anhydrous magnesium sulfate and concentrated in vacuo. The oily residue was purified by silica gel column chromatography to give 1.03 g (40%) of the titled compound No.7-1 and 0.48 g (19%) of the titled compound No.7-2.

(compound No.7-1)

IR (film, $cm^{-1}$) 3029, 2967, 1692, 1660, 1454, 1418, 1306, 1191, 1123, 927, 810, 704.

(compound No.7-2)

IR (film, $cm^{-1}$) 3028, 2969, 1673, 1454, 1410, 1250, 1121, 958, 744, 704.

Example 8

2,4-bis(4-methoxybenzylthiomethyl)-4-butanolide

To a stirred solution of 4-methoxybenzylmercaptane (0.47 ml) in THF (6 ml), n-butyllithium/n-hexane (1.6N, 0.18 ml) and 4-(4-methoxybenzylthiomethyl)- 2-methylene-4-butanolide (compound No.1- 2, 0.76 g) dissolved in THF (4 ml) was added dropwise at about −78° C. under nitrogen atmosphere. The mixture was stirred for an additional 15 minutes at −78° C. After restoring to room temperature, saturated aqueous ammonium chloride solution was added to the mixture. The mixture was acidified with 1N hydrochloric acid and extracted with ethyl acetate. The organic layer was washed with water and saturated sodium chloride solution. The organic layer was dried over anhydrous sodium sulfate and concentrated in vacuo to give crude oil of the titled compound as a mixture of cis and trans forms. The ratio of cis and trans products is 2.2:1.0.

cis-form (compound No.8-1)

mp 77.5°–79.2° C. (n-hexane—ethyl acetate)

IR (KBr, $cm^{-1}$) 2912, 1763, 1609, 1514, 1458, 1445, 1306, 1242, 1177, 1025, 994, 835, 824.

trans-form (compound No.8-2)

mp 67.1°–67.8° C. (n-hexane—ethyl acetate)

IR (KBr, $cm^{-1}$) 2936, 2908, 1762, 1609, 1514, 1457, 1445, 1305, 1242, 1176, 1026, 836, 824.

By substituting starting materials, the following compounds can be prepared by the similar method as Example 8.

4-(1-benzylthio-1-methylethyl)-2-benzylthiomethyl-4-butanolide cis-form (compound No.8-3)

IR (film, $cm^{-1}$) 1768, 1601, 1495, 1452, 1169, 969, 733, 703.

trans-form (compound No.8-4)

IR (film, $cm^{-1}$) 1765, 1601, 1495, 1452, 1186, 1158, 997, 733, 703.

4-[1-(4-methoxybenzylthio)-1-methylethyl]-2-(4-methoxybenzylthiomethyl)- 4-butanolide cis-form (compound No.8-5)

IR (film, $cm^{-1}$) 1770, 1610, 1512, 1464, 1301, 1246, 1174, 1032, 834.

trans-form (compound No.8-6)

IR (film, $cm^{-1}$) 1758, 1609, 1515, 1252, 1235, 1167, 1031, 846.

cis-2,4-bis(benzylthiomethyl)-4-butanolide (compound No.8-7)

IR (film, $cm^{-1}$) 3027, 2919, 1770, 1601, 1494, 1453, 1346, 1169, 1011, 917, 770, 703.

cis-4-(1-benzylthio-1-methylethyl)-2-benzylthiomethyl-3-methoxycarbonyl- 4-butanolide (compound No.8-8)

mp 84.8°–86.1° C. (n-hexane—ethyl acetate).

IR (KBr, $cm^{-1}$) 2969, 2931, 1767, 1721, 1602, 1494, 1454, 1439, 1326, 1261, 1186, 1167, 998, 698.

cis-4-(1-tritylthio-1-methylethyl)-2-tritylthiomethyl-4-butanolide (compound No.8-9)

IR (film, $cm^{-1}$) 3055, 1775, 1594, 1490, 1444, 1166, 742, 700.

2,4-bis(tert-butylthiomethyl)-4-butanolide (compound No.8-10)

IR (film, $cm^{-1}$) 2961, 1775, 1460, 1365, 1198, 1161, 1008.

2-tert-butylcarbonylthiomethyl-4-(1-tert-butylcarbonylthio-1-methylethyl)- 4-butanolide (compound No.8-11)

IR ($CHCl_3$, $cm^{-1}$) 3019, 2972, 1771, 1723, 1676, 1477, 1367, 938.

4-(2-benzylthioethyl)-2-benzylthiomethyl-4-butanolide (compound No.8-12)

4-(3-benzylthiopropyl)-2-benzylthiomethyl-4-butanolide (compound No.8-13)

4-(4-benzylthiobutyl)-2-benzylthiomethyl-4-butanolide (compound No.8-14)

4-(2-benzylthio-1-methylethyl)-2-benzylthiomethyl-4-butanolide (compound No.8-15)

4-(1-benzylthio-1-ethylpropyl)-2-benzylthiomethyl-4-butanolide (compound No.8-16)

4-(1-benzylthio-1-methylethyl)-2-(1-benzylthioethyl)-4-butanolide (compound No.8-17)

4-(1-benzylthio-1-methylethyl)-2-benzylthiomethyl-3-methyl-4-butanolide (compound No.8-18)

2,4-bis(4-methylbenzylthiomethyl)-4-butanolide (compound No.8-19)

Example 9

2,4-bis(mercaptomethyl)-4-butanolide

1) Into a solution of 2,4-bis(4-methoxybenzylthioethyl)-4-butanolide (mixture of cis and trans forms, 2.40 g) in a mixture of methanol (30 ml) and THF (10 ml), ammonia gas was bubbled for 30 minutes under ice-cooling. The mixture was stirred overnight at room temperature and concentrated in vacuo. The oily residue was purified by silica gel column chromatography to give 2.36 g (94%) of the following compound.

4-hydroxy-5-(4-methoxybenzylthio)-2-(4-methoxybenzylthiomethyl)pentanamide

IR (film, $cm^{-1}$) 3340, 3192, 2912, 1664, 1610, 1511, 1439, 1301, 1245, 1176, 1032, 832, 735.

2) A solution of the amide compound (2.36 g) prepared above in THF (8 ml) was added to liquid ammonia (50 ml), and sodium metal was added to the solution in a small portion under nitrogen atmosphere while stirring. After the reaction was completed, ammonium chloride was added to the mixture and ammonia was evaporated. To the residue, THF (10 ml) and 2N hydrochloric acid (10 ml) were added, and the mixture was stirred overnight at room temperature. The mixture was concentrated in vacuo and extracted with ethyl acetate. The organic layer was washed with water and saturated sodium chloride. The organic layer was dried over anhydrous sodium sulfate and concentrated in vacuo. The oily residue was purified by silica gel column chromatography to give 0.16 g (17%) of cis-form, 0.16 g (17%) of trans-form and 0.19 g (20%) of cis-trans mixture of the titled compound.

cis-form (compound No.9-1)

IR (film, cm$^{-1}$) 2936, 2564, 1770, 1449, 1416, 1349, 1296, 1168, 1008, 953, 897, 728.

trans-form (compound No.9-2)

IR (film, cm$^{-1}$) 2936, 2560, 1763, 1417, 1350, 1289, 1167, 1034, 987, 959.

By substituting starting materials, the following compound was prepared by the similar method as Example 9-1).

5-benzylthio-2-benzylthiomethyl-4-hydroxy-5-methylhexanamide

IR (film, cm$^{-1}$) 3336, 3192, 1666, 1602, 1496, 1453, 1299, 1070, 702.

The following compounds were prepared by the similar method as Example 9-2) using the above compound.

4-(1-mercapto-1-methylethyl)-2-mercaptomethyl-4-butanolide cis-form (compound No.9-3)

IR (film, cm$^{-1}$) 2564, 1767, 1462, 1347, 1193, 1168, 1003, 974.

trans-form (compound No.9-4)

IR (film, cm$^{-1}$) 2560, 1767, 1459, 1344, 1165, 1049, 1003.

By substituting starting materials, the following compounds can be prepared by the similar methods as Example 9-1) and 9-2).

4-(2-mercaptoethyl)-2-mercaptomethyl-4-butanolide (compound No. 9-5)

4-(3-mercaptopropyl)-2-mercaptomethyl-4-butanolide (compound No.9-6)

4-(3-mercaptobutyl)-2-mercaptomethyl-4-butanolide (compound No.9-7)

4-(2-mercapto-1-methylethyl)-2-mercaptomethyl-4-butanolide (compound No.9-8)

4-(1-mercapto-1-ethylpropyl)-2-mercaptomethyl-4-butanolide (compound No.9-9)

4-(1-mercapto-1-methylethyl)-2-(1-mercaptoethyl)-4-butanolide (compound No.9-10)

4-(1-mercapto-1-methylethyl)-3-methyl-2-mercaptomethyl-4-butanolide (compound No.9-11)

Example 10

4-(1-benzylthio-1-methylethyl)-2-benzylthiomethyl-4-butanolide

To a stirred solution of benzylmercaptane (0.40 ml) in THF (5 ml), n-butyllithium/n-hexane (1.6N, 0.10 ml) was added dropwise under nitrogen atmosphere and ice-cooling. After 5 minutes, 5-benzylthio-4-hydroxy-5-methyl-2-methylenehexanoic acid methyl ester (1.00 g) dissolved in THF (5 ml) was added to the mixture. The mixture was stirred for an additional 1 hour and saturated aqueous ammonium chloride solution (1 ml) was added to the mixture. The mixture was extracted with ether. The organic layer was dried over anhydrous sodium sulfate and concentrated in vacuo. The oily residue was purified by silica gel column chromatography to give 0.83 g (63%) of cis-form, 0.41 g (31%) of trans-form of the titled compound.

Physical data of cis and trans forms were identical with that of compound No.8-3 and No.8-4 prepared by Example 8.

Example 11 cis-4-(1-acetylthio-1-methylethyl)-2-acetylthiomethyl-4-butanolide (compound No.11-1)

To a stirred solution of cis-4-(1-mercapto-1-methylethyl)-2-mercaptomethyl- 4-butanolide (compound No.9-3, 0.102 g) in methylene chloride (3 ml), triethylamine (0.20 ml) and acetyl chloride (0.10 ml) were added and stirred for 30 minutes under nitrogen atmosphere and ice-cooling. The mixture was poured into saturated aqueous ammonium chloride solution (30 ml) and extracted with ether. The organic layer was washed with saturated aqueous ammonium chloride solution and saturated sodium chloride solution, dried over anhydrous sodium sulfate and concentrated in vacuo. The oily residue was purified by silica gel column chromatography to give 0.133 g (93%) of the titled compound.

IR (film, cm$^{-1}$) 1774, 1688, 1354, 1172, 1133, 1111, 999, 972, 952, 625.

By substituting starting materials, the following compounds can be prepared by the similar methods as Example 11.

cis-4-(1-benzoylthio-1-methylethyl)-2-benzoylthiomethyl-4-butanolide (compound No.11-2)

IR (film, cm$^{-1}$) 2974, 1776, 1660, 1206, 1175, 911, 689.

2,4-bis (4-methylbenzoylthiomethyl)-4-butanolide (compound No.11-3)

2,4-bis(4-methoxybenzoylthiomethyl)-4-butanolide (compound No.11-4)

Example 12

4-(1-allylthio-1-methylethyl)-2-allylthiomethyl-4-butanolide

To a solution of 4-(1-mercapto-1-methylethyl)-2-mercaptomethyl- 4-butanolide (0.24 g) in methylene chloride (3 ml), allyl bromide (1.0 ml) and N,N-(diisopropyl)ethylamine (1.0 ml) were added under nitrogen atmosphere. The mixture was stirred overnight at room temperature. The mixture was diluted with ether (50 ml) and washed with 2N hydrochloric acid and saturated sodium chloride solution. The organic layer was dried over anhydrous sodium sulfate and concentrated in vacuo. The oily residue was purified by silica gel column chromatography to give 0.142 g (43%) of cis-form (compound No.12-1) and 0.170 g (51%) of trans-form (compound No.12-2) of the titled compound.

cis-form (compound No.12-1)

IR (film, cm$^{-1}$) 1771, 1635, 1170, 992, 972, 920.

trans-form (compound No.12-2)

IR (film, cm$^{-1}$) 1771, 1635, 1159, 990, 920.

By substituting starting materials, the following compound can be prepared by the similar methods as Example 12.

cis-4-(1-methylthio-1-methylethyl)-2-methylthiomethyl-4-butanolide (compound No.12-3)

IR (film, cm$^{-1}$) 2972, 2921, 1770, 1428, 1345, 1292, 1172, 1057, 999, 971.

Example 13

4-[1-methyl-1-(2-tetrahydropyranylthiomethyl)ethyl]-2-(2-tetrahydropyranylthiomethyl)-4-butanolide (compound No.13-1)

To a solution of 4-(1-mercapto-1-methylethyl)-2-mercaptomethyl- 4-butanolide (103 mg) in dry ether (2 ml), dihydropyran (110 mg) dissolved in dry ether (2 ml) and boron trifluoride diethyl ether complex (15 mg) dissolved in dry ether (1 ml) were added in the order named to the mixture under nitrogen atmosphere. The mixture was stirred overnight at room temperature. The mixture was diluted with benzene and ethyl acetate, and washed with 10% aqueous solution of sodium bicarbonate, water and saturated sodium chloride solution. The organic layer was dried over anhydrous sodium sulfate and concentrated in vacuo. The oily residue was purified by silica gel column chromatography to give 152 mg (81%) of the titled compound.

IR (film, cm$^{-1}$) 2938, 2860, 1770, 1188, 1170, 1036, 1006.

Example 14

N-benzyl-4-[1-(4-methoxybenzylthio)-1-methylethyl]-2-(4-methoxybenzylthiomethyl)-4-butanelactam To a stirred solution of 4-methoxybenzylmercaptane (2.98 ml) in THF (30 ml), n-butyllithium/n-hexane (1.6N, 5.73 ml) was added under nitrogen atmosphere and ice-cooling. After 10 minutes, N-benzyl-4-[1-(4-methoxybenzylthio)-1-methylethyl]-2-methylene-4-butanelactam (compound No.5-1, 7.00 g) dissolved in THF (20 ml) was added dropwise to the mixture and the mixture was stirred for additional 30 minutes under ice-cooling. Ammonium chloride was added to the mixture and the mixture was concentrated in vacuo. Water and ethyl acetate were added to the residue and the organic layer was separated. The organic layer was washed with saturated sodium chloride solution, dried over anhydrous sodium sulfate and concentrated in vacuo. The oily residue was purified by silica gel column chromatography to give 9.66 g (98.3%) of the titled compound as a mixture of cis and trans forms. The ratio of cis and trans form is 5.7:1. Cis-form product was isolated as crystal from the mixture.

cis-form (compound No.14-1)
mp 92.8°–94.8° C. (n-hexane—ethyl acetate).
IR (KBr, cm$^{-1}$) 2964, 2928, 1677, 1609, 1510, 1406, 1300, 1239, 1174, 1029, 837, 732.

By substituting starting materials, the following compounds can be prepared by the similar methods as Example 14.

cis-N-benzyl-4-(1-benzylthio-1-methylethyl)-2-benzylthiomethyl-4-butanelactam (compound No.14-2)
mp 108.2°–109.3° C. (n-hexane—ethyl acetate)
IR (KBr, cm$^{-1}$) 3030, 1683, 1494, 1400, 1248, 1152, 952, 774, 747, 711.

4-(1-benzylthio-1-methylethyl)-2-benzylthiomethyl-N-ethoxycarbonylmethyl- 4-butanelactam (compound No.14-3)
IR (film, cm$^{-1}$) 2976, 2932, 1742, 1694, 1602, 1494, 1454, 1392, 1374, 1202, 1028, 960, 770, 709.

cis-N-benzyl-4-(1-benzylthio-1-methylethyl)-2-benzylthiomethyl-3-methyl- 4-butanelactam (compound No.14-4)
IR (film, cm$^{-1}$) 3028, 2965, 2923, 1682, 1602, 1494, 1454, 1417, 1240, 1070, 1029, 702.

cis-4-(1-benzylthio-1-methylethyl)-2-benzylthiomethyl-N-(5-tertbutoxycarbonylaminopentyl)- 4-butanelactam (compound No.14-5)
IR (film, cm$^{-1}$) 3340, 2973, 2930, 2862, 1681, 1514, 1454, 1365, 1250, 1171, 868, 770, 711.

cis-4-(1-benzylthio-1-methylethyl)-2-benzylthiomethyl-N-(4-methoxycarbonylbenzyl)- 4-butanelactam (compound No.14-6)
IR (film, cm$^{-1}$) 3436, 2971, 1719, 1687, 1279, 753, 705.

cis-N-benzyloxy-2,4-bis(benzylthiomethyl)-4-butanelactam (compound No.14-7)
mp 57.2°–58.1° C. (isopropyl ether—ethyl acetate).
IR (KBr, cm$^{-1}$) 3031, 2920, 1702, 1494, 1453, 1364, 1230, 1026, 978, 754, 700.

cis-2,4-bis(benzylthiomethyl)-N-methoxy-4-butanelactam (compound No.14-8)
IR (film, cm$^{-1}$) 3027, 2935, 1714, 1601, 1494, 1453, 1353, 1240, 1038, 984, 770, 704.

trans-2,4-bis(benzylthiomethyl)-N-methoxy-4-butanelactam (compound No.14-9)
IR (film, cm$^{-1}$) 3027, 2918, 1714, 1601, 1494, 1453, 1353, 1241, 1047, 979, 770, 703.

N-benzyl-2,4-bis(benzylthiomethyl)-4-butanelactam (compound No.14-10)
IR (film, cm$^{-1}$) 3027, 2917, 1688, 1602, 1494, 1453, 1418, 1362, 1245, 702.

cis-2,4-bis(benzylthiomethyl)-N-isopropyl-4-butanelactam (compound No.14-11)
IR (film, cm$^{-1}$) 2970, 2920, 1681, 1494, 1453, 1418, 1355, 1071, 769, 703.

trans-2,4-bis(benzylthiomethyl)-N-isopropyl-4-butanelactam (compound No.14-12)
IR (film, cm$^{-1}$) 2969, 2929, 1682, 1494, 1453, 1417, 1365, 1269, 1225, 1129, 1071, 769, 703.

cis-N-benzyl-4-(2-benzylthio-2-methylpropyl)-2-benzylthiomethyl- 4-butanelactam (compound No.14-13)
mp 59.1°–60.2° C. (isopropyl ether—ethyl acetate).
IR (KBr, cm$^{-1}$) 1679, 1494, 1433, 1270, 1196, 1120, 1070, 1024, 938, 768, 720, 698.

trans-N-benzyl-4-(2-benzylthio-2-methylpropyl)-2-benzylthiomethyl- 4-butanelactam (compound No.14-14)
mp 108.5°–109.2 ° C. (isopropyl ether—ethyl acetate).
IR (KBr, cm$^{-1}$) 2968, 1679, 1495, 1453, 1364, 1257, 1167, 1072, 1028, 940, 755, 699, 670.

N-benzyl-4-(3-benzylthiopropyl)-2-benzylthiomethyl-4-butanelactam (compound No.14-15)

N-benzyl-4-(4-benzylthiobutyl)-2-benzylthiomethyl-4-butanelactam (compound No.14-16)

N-benzyl-4-(2-benzylthio-1-methylethyl)-2-benzylthiomethyl-4-butanelactam (compound No.14-17)

N-benzyl-4-(1-benzylthio-1-ethylpropyl)-2-benzylthiomethyl-4-butanelactam (compound No.14-18)

N-benzyl-4-(1-benzylthio-1-methylethyl)-2-benzylthiomethyl-3-methoxycarbonyl- 4-butanelactam (compound No.14-19)

N-benzyl-2-benzylthiomethyl-4-(1-methylthio-1-methylethyl)-4-butanelactam (compound No.14-20)

N-benzyl-4-(1-allylthio-1-methylethyl)-2-benzylthiomethyl-4-butanelactam (compound No.14-21)

N-benzyl-2-benzylthiomethyl-4-[1-(4-methylbenzylthio)-1-methylethyl] -4-butanelactam (compound No.14-22)

N-benzyl-4-(1-benzylthio-1-methylethyl)-2-(1-benzylthioethyl)-4-butanelactam (compound No.14-23)

N-(5-benzylaminopentyl)-4-(1-benzylthio-1-methylethyl)-2-benzylthiomethyl- 4-butanelactam (compound No.14-24)

4-(1-benzylthio-1-methylethyl)-2-benzylthiomethyl-N-(5-dimethylaminopentyl)- 4-butanelactam (compound No.14-25)
4-(1-benzylthio-1-methylethyl)-2-benzylthiomethyl-N-(4-methylbenzyl)-4-butanelactam (compound No.14-26)
4-(1-benzylthio-1-methylethyl)-2-benzylthiomethyl-N-(4-methoxybenzyl)-4-butanelactam (compound No.14-27)
4-(1-benzylthio-1-methylethyl)-2-benzylthiomethyl-N-(4-chlorobenzyl)- 4-butanelactam (compound No.14-28)
4-(1-benzylthio-1-methylethyl)-2-benzylthiomethyl-N-(4-methylbenzyloxy)-4-butanelactam (compound No.14-29)
4-(1-benzylthio-1-methylethyl)-2-benzylthiomethyl-N-(4-methoxybenzyloxy)-4-butanelactam (compound No.14-30)
4-(1-benzylthio-1-methylethyl)-2-benzylthiomethyl-N-(4-chlorobenzyloxy)- 4-butanelactam (compound No.14-31)
N-benzyl-2-benzylthiomethyl-4-(1-tritylthio-1-methylpropyl)-4-butanelactam (compound No.14-32)

Example 15 cis-N-benzyl-4-(1-mercapto-1-methylethyl)-2-mercaptomethyl-4-butanelactam (compound No.15-1)

To a stirred solution of cis-N-benzyl-4-[1-(4-methoxybenzylthio)- 1-methylethyl]-2-(4-methoxybenzylthiomethyl)-4-butanelactam (compound No.14-1, 500 mg) in trifluoroacetic acid (4 ml), thioanisol (0.66 ml) and trifluoromethanesulfonic acid (0.50 ml) were added. After stirring for 2 hours at room temperature, the mixture was poured into a mixture of ice and saturated aqueous sodium bicarbonate solution and extracted with ethyl acetate. The organic layer was washed with saturated aqueous sodium bicarbonate solution, water and then saturated sodium chloride solution. The organic layer was dried over anhydrous magnesium sulfate and concentrated in vacuo. The oily residue was dissolved in ethanol (3 ml). To the solution sodium borohydride (20 mg) was added and the mixture was stirred for 30 minutes at room temperature. 1N hydrochloric acid was added to the mixture and extracted with ethyl acetate. The organic layer was washed with water and saturated sodium chloride solution, dried over anhydrous magnesium sulfate and concentrated in vacuo. The oily residue was purified by silica gel column chromatography to give 50 mg (18%) of the titled compound.

IR (film, cm$^{-1}$) 2968, 2928, 2868, 2550, 1679, 1497, 1408, 1251, 1166, 733, 700.

By substituting starting materials, the following compounds can be prepared by the similar methods as Example 15.
N-benzyl-2,4-bis(mercaptomethyl)-4-butanelactam (compound No.15- 2)
IR (film, cm$^{-1}$) 2930, 2555, 1682, 1495, 1427, 1360, 1305, 1081, 737, 703.
cis-N-(4-carboxybenzyl)-4-(1-mercapto-1-methylethyl)-2-mercaptomethyl-4-butanelactam (compound No.15-3)
IR (film, cm$^{-1}$) 2971, 2620, 2570, 2503, 1682, 1613, 1410, 1257, 1177, 1021, 752.

Example 16 cis-4-(1-mercapto-1-methylethyl)-2-mercaptomethyl-4-butanelactam (compound No.16-1)

A solution of cis-N-benzyl-4-[1-(4-methoxybenzylthio)-1-methylethyl] -2-(4-methoxybenzylthiomethyl)-4-butanelactam (compound No.14-1, 0.40 g) in THF (8 ml) was added in liquid ammonia (60 ml). To the solution sodium metal (0.12 g) was added in a small portion under nitrogen atmosphere. After an addition of ammonium chloride, ammonia was evaporated and a product was extracted with ethyl acetate. The organic layer was washed with water and saturated sodium chloride solution, dried over anhydrous sodium sulfate and concentrated in vacuo. The separated crystals were filtered to give 70 mg (46%) of the titled compound.

mp 158.8°–160.6° C. (ethyl acetate—methanol).

IR (KBr, cm$^{-1}$) 3188, 3076, 2968, 2864, 1691, 1390, 1375, 1298, 1257, 1143, 791.
trans-4-(1-mercapto-1-methylethyl)-2-mercaptomethyl-4-butanelactam (compound No.16-1)
The compound was prepared from trans-N-benzyl-4-[1-(4-methoxybenzylthio)- 1-methylethyl]-2-(4-methoxybenzylthiomethyl)-4-butanelactam, which contained 20% of cis-form, by the similar method described above.

mp 105.8°–107.7° C. (n-hexane—ethyl acetate).

IR (KBr, cm$^{-1}$) 3192, 3080, 2964, 2928, 1683, 1453, 1389, 1296, 1262, 802.

By substituting starting materials, the following compounds can be prepared by the similar methods as Example 16.
cis-N-carboxymethyl-4-(1-mercapto-1-methylethyl)-2-mercaptomethyl- 4-butanelactam (compound No.16-3)
mp 104.7°–105.5° C. (isopropylether—ethyl acetate).
IR (KBr, cm$^{-1}$) 1750, 1649, 1430, 1370, 1352, 1295, 1266, 1199, 1126, 1074, 932, 852.
cis-4-(1-mercapto-1-methylethyl)-2-mercaptomethyl-3-methyl-4-butanelactam (compound No.16-4)
mp 116.4°–118.8° C. (n-hexane—ethyl acetate).
IR (KBr, cm$^{-1}$) 3202, 3093, 2963, 2559, 1694, 1461, 1387, 1330, 1251, 1144, 1003, 792.
cis-N-(5-tert-butoxycarbonylaminopentyl)-4-(1-mercapto-1-methylethyl)- 2-mercaptomethyl-4-butanelactam (compound No.16-5)
IR (film, cm$^{-1}$) 3341, 2974, 2932, 2864, 2546, 1682, 1520, 1455, 1418, 1366, 1251, 1172, 868, 736.
cis-2,4-bis(mercaptomethyl)-4-butanelactam (compound No.16-6)
IR (film, cm$^{-1}$) 3228, 2926, 2551, 1682, 1426, 1382, 1345, 1301, 1265, 1078, 913, 730.
2,4-bis(mercaptomethyl)-4-butanelactam (compound No.16-7)
IR (film, cm$^{-1}$) 2926, 2552, 1682, 1454, 1428, 1383, 1344, 1269, 1071, 702.
cis-2,4-bis(mercaptomethyl)-N-isopropyl-4-butanelactam (compound No.16-8)
IR (film, cm$^{-1}$) 3469, 2970, 2932, 2545, 1674, 1422, 1364, 1271, 1217, 1130.
trans-2,4-bis(mercaptomethyl)-N-isopropyl-4-butanelactam (compound No.16-9)
IR (film, cm$^{-1}$) 3480, 2970, 2933, 2545, 1682, 1424, 1366, 1275, 1224, 1130, 1069, 714.
cis-4-(2-mercapto-2-methylpropyl)-2-mercaptomethyl-4-butanelactam (compound No.16-10)
mp 107.9°–111.7° C. (isopropylether—ethyl acetate).
IR (KBr, cm$^{-1}$) 3188, 3081, 2972, 2516, 1693, 1456, 1384, 1365, 1296, 1248, 1121, 804, 702.
4-(3-mercaptopropyl )-2-mercaptomethyl-4-butanelactam (compound No.16-11)
4-(4-mercaptobutyl )-2-mercaptomethyl-4-butanelactam (compound No.16-12)
4-(2-mercapto-1-methylethyl)-2-mercaptomethyl-4-butanelactam (compound No.16-13)
4-(1-mercapto-1-ethylpropyl)-2-mercaptomethyl-4-butanelactam (compound No.16-14)

N-(5-dimethylaminopentyl)-(1-mercapto-1-methylethyl)-2-mercaptomethyl- 4-butanelactam (compound No.16-15)

Example 17 cis-4-(1-benzylthio-1-methylethyl)-2-benzylthiomethyl-N-carboxymethyl- 4-butanelactam (compound No.17-1)

To a solution of 4-(1-benzylthio-1-methylethyl)-2-benzylthiomethyl-N-ethoxycarbonylmethyl- 4-butanelactam (compound No.14- 3, 1.50 g) in methanol (20 ml), 2N—KOH (6.4 ml) was added and the mixture was stirred for 1.5 hours at room temperature. The mixture was acidified with dilute hydrochloric acid and concentrated in vacuo. A product was extracted with ethyl acetate. The organic layer was washed with water and saturated sodium chloride solution. The organic layer was dried over anhydrous magnesium sulfate and concentrated in vacuo to give 0.94 g (67%) of the titled compound.

mp 116.6°–117.7° C. (isopropylether—ethyl acetate).

IR (KBr, cm$^{-1}$) 3023, 2966, 1693, 1495, 1455, 1385, 1298, 1247, 1168, 1069, 916, 769, 699.

By substituting starting materials, the following compound can be prepared by the similar methods as Example 17.

cis-4-(1-benzylthio-1-methylethyl)-2-benzylthiomethyl-N-(4-carboxybenzyl)- 4-butanelactam (compound No.17-2)
mp 177.6°–179.2° C.

IR (KBr, cm$^{-1}$) 3029, 2971, 2886, 1703, 1639, 1418, 1406, 1265, 748, 704.

Example 18 cis-N-(5-aminopentyl)-4-(1-mercapto-1-methylethyl)-2-mercaptomethyl- 4-butanelactam hydrochloride (compound No.18-1)

To a solution of cis-N-(5-tert-butoxycarbonylaminopentyl)-4-( 1-mercaptomethyl-1-methylethyl)-2-mercaptomethyl-4-butanelactam (compound No.16-5, 0.40 g) in THF (4 ml), hydrogen chloride/dioxane (6.5N, 0.95 ml) was added and the mixture was stirred overnight at room temperature. The mixture was concentrated in vacuo. The oily residue was purified by silica gel column chromatography to give 0.12 g (40%) of the titled compound.

IR (film, cm$^{-1}$) 3428, 2968, 2538, 1664, 1459, 1391, 1248, 1121, 754, 664.

Example 19

N-benzyl-2,4-bis(methylthiomethyl)-4-butanelactam (compound No.19-1)

N-benzyl-2,4-bis(mercaptomethyl)-4-butanelactam (compound No. 15-2, 0.53 g), potassium carbonate (0.32 g) and methyl iodide (0.21 ml) are added to ethanol (5 ml) and the mixture is stirred for 4 hours at room temperature. Ether (100 ml) is added to the mixture. The organic layer is washed with water and saturated sodium chloride solution. The organic layer is dried over anhydrous sodium sulfate and concentrated in vacuo. The oily residue is purified by silica gel column chromatography to give the titled compound.

By substituting starting materials, the following compound can be prepared by the similar methods as Example 19.

N-benzyl-2,4-bis(allylthiomethyl)-4-butanelactam (compound No.19- 2)

Example 20

N-benzyl-2,4-bis(acetylthiomethyl)-4-butanelactam (compound No.20-1)

To a stirred solution of N-benzyl-2,4-bis(mercaptomethyl)-4-butanelactam (compound No.15-2, 0.27 g) and triethylamine (0.40 ml) in methylene chloride (10 ml), acetyl chloride (0.20 ml) is added. The mixture is stirred for 30 minutes under nitrogen atmosphere and ice-cooling, and poured into saturated aqueous ammonium chloride solution (50 ml) and extracted with ether. The organic layer is washed with saturated aqueous ammonium chloride solution and saturated sodium chloride solution. The solution is dried over anhydrous sodium sulfate and concentrated in vacuo. The oily residue is purified by silica gel column chromatography to give the titled compound.

By substituting starting materials, the following compounds can be prepared by the similar methods as Example 20.

N-benzyl-2,4-bis(benzoylthiomethyl)-4-butanelactam (compound No.20-2)
N-benzyl-2,4-bis(4-methylbenzoylthiomethyl)-4-butanelactam (compound No.20-3)
N-benzyl-2,4-bis(4-methoxybenzoylthiomethyl)-4-butanelactam (compound No.20-4)

Example 21

N-benzyl-2,4-bis(2-tetrahydropyranylthiomethyl)-4-butanelactam (compound No.21-1)

To a solution of N-benzyl-2,4-bis(mercaptomethyl)-4-butanelactam (compound No.15-2, 134 mg) in dry ether (2 ml), dihydropyran (110 mg) dissolved in dry ether (2 ml) is added under nitrogen atmosphere and then boron trifluoride diethyl ether complex (15 mg) dissolved in dry ether (1 ml) is added to the mixture. The mixture is stirred overnight at room temperature. The mixture is diluted with a mixture of benzene and ethyl acetate and washed with 10% aqueous sodium bicarbonate solution, water and saturated sodium chloride solution. The organic layer is dried over anhydrous sodium sulfate and concentrated in vacuo. The oily residue is purified by silica gel column chromatography to give the titled compound.

[Formulation Example]

Examples of the formulation containing the compound of this invention of the formula [I] are shown below.

| (Tablet) | |
| --- | --- |
| compound of this invention | 1 mg |
| lactose | 105 mg |
| corn starch | 38 mg |
| silicone dioxide | 15 mg |
| low-substituted hydroxypropylcellulose | 5 mg |
| hydroxypropylcellulose - L | 5 mg |
| magnesium stearate | 1 mg |
| total | 170 mg |
| compound of this invention | 5 mg |
| lactose | 155 mg |
| corn starch | 58 mg |
| silicone dioxide | 30 mg |
| low-substituted hydroxypropylcellulose | 10 mg |

| | |
|---|---|
| hydroxypropylcellulose - L | 10 mg |
| magnesium stearate | 2 mg |
| total (Soft capsule) | 270 mg |
| compound of this invention | 50 mg |
| vegetable oil | 150 mg |
| gelatin | 140 mg |
| total | 340 mg |

PHARMACOLOGICAL TEST

Thymulin-like activities of the compound of this invention were examined by modifying the method reported by J. F. Bach et al. (Bull. Inst. Pasteur, 76, 325 (1978)).

(Experimental Method)

A thymus of C57BL/6 strain male mouse (10 weeks age, 4 mice a group) was removed. After about two weeks, a spleen of the mouse was extracted and a spleen cells suspension ($1\times10^8$ cells/ml in Hank's solution) was prepared. To 100 µl of the cells suspension, 100 µl of Hank's solution dissolving a test compound and zinc chloride in 1:1 molar ratio was added. After a 30 minutes incubation at 37° C., 50 µl of azathiopurine (50 µg/ml in Hank's solution) was added and the mixture was incubated further for 60 minutes at the same temperature. To the mixture, 50 µl of sheep red blood cells ($1\times10^8$ cells/ml in Hank's solution ) was added and mixed. The mixture was incubated at 4° C. for one night. After gently shaking, E-rosette forming cells (E-RFC) were measured. As an active control, a solution of thymulin and zinc chloride, which were dissolved in Hank's solution in a concentration of $1\times10^{-14}$M and 1:1 molar ratio, was used and it was treated in the same manner as the case of the test compound.

(Result)

Thymulin-like activity was calculated by the following formula.

$$\frac{(E\text{-}RFC \text{ of a test compound}) - (E\text{-}RFC \text{ of a control})}{(E\text{-}RFC \text{ of an active control}) - (E\text{-}RFC \text{ of a control})} \times 100(\%)$$

Thymulin-like activities of some typical examples of the compounds of this invention were measured. Each compound showed more than 50% of the thymulin-like activity at a concentration of lower than $10^{-7}$M. Especially the compounds having thiol groups on the side chains, for example the compounds shown in Example 9, 15, 16 etc., showed excellent activities. The compounds having thiol groups protected by methyl, benzyl, etc., also showed excellent activities.

INDUSTRIAL APPLICABILITY

This invention offers novel compounds which are useful for treatment of diseases such as immunodeficiency and autoimmune diseases caused by various immune disorders, and synthetic intermediates therefor.

What we claim is:

1. A compound of the formula (I) and pharmaceutically acceptable salts thereof,

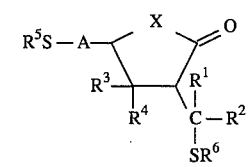

wherein $R^1$ and $R^2$ are the same or different and each is hydrogen or $C_1$–$C_6$ alkyl;

$R^3$ and $R^4$ are the same or different and each is hydrogen, $C_1$–$C_6$ alkyl, carboxy or $C_1$–$C_6$ alkoxycarbonyl;

$R^5$ and $R^6$ are the same or different and each is hydrogen, $C_1$–$C_6$ alkyl, $C_2$–$C_6$ alkenyl, $C_2$–$C_6$ alkanoyl, phenyl $C_1$–$C_6$ alkyl, phenylcarbonyl, trityl or tetrahydropyranyl, and the phenyl ring of said phenyl $C_1$–$C_6$ alkyl or phenylcarbonyl is unsubstituted or substituted by $C_1$–$C_6$ alkyl, $C_1$–$C_6$ alkoxy, halogen, carboxy or $C_1$–$C_6$ alkoxycarbonyl;

X is oxygen or $NR^7$;

$R^7$ is hydrogen, $C_1$–$C_6$ alkyl, $C_1$–$C_6$ alkoxy, phenyl $C_1$–$C_6$ alkyl or phenyl $C_1$–$C_6$ alkoxy, and said alkyl group is unsubstituted or substituted by carboxy, $C_1$–$C_6$ alkoxycarbonyl, amino, $C_1$–$C_6$ alkylamino, $C_1$–$C_6$ alkoxycarbonylamino or phenyl $C_1$–$C_6$ alkylamino, and the phenyl ring of said phenyl $C_1$–$C_6$ alkyl, phenyl $C_1$–$C_6$ alkoxy, or phenyl $C_1$–$C_6$ alkylamino is unsubstituted or substituted by $C_1$–$C_6$ alkyl, $C_1$–$C_6$ alkoxy, halogen, carboxy or $C_1$–$C_6$ alkoxycarbonyl, and A is straight or branched $C_1$–$C_6$ alkylene.

2. The compound as in claim 1, wherein $R^1$ and $R^2$ are the same or different and each is hydrogen or methyl;

$R^3$ and $R^4$ are the same or different and each is hydrogen, methyl, carboxy or methoxycarbonyl;

$R^5$ and $R^6$ are the same or different and each is hydrogen, methyl, isopropyl, allyl, acetyl, pivaloyl, benzyl, methylbenzyl, methoxybenzyl, benzoyl, methylbenzoyl, methoxybenzoyl, trityl or tetrahydropyranyl;

$R^7$ is hydrogen, isopropyl, carboxymethyl, ethoxycarbonylmethyl, aminopentyl, dimethylaminopentyl, t-butoxycarbonylaminopentyl, benzylaminopentyl, methoxy, benzyl, methylbenzyl, methoxybenzyl, chlorobenzyl, carboxybenzyl, methoxycarbonylbenzyl, benzyloxy, methylbenzyloxy, methoxybenzyloxy or chlorobenzyloxy, and A is methylene, ethylene, trimethylene, tetramethylene, (dimethyl)methylene, (diethyl)methylene, (methyl)ethylene or (dimethyl)ethylene.

3. The compound as in claim 1, wherein $R^1$, $R^2$, $R^3$, $R^4$, $R^5$ and $R^6$ are hydrogen, and X is oxygen.

4. The compound as in claim 1, wherein X is $NR^7$, and $R^1$, $R^2$, $R^3$, $R^4$, $R^5$, $R^6$ and $R^7$ are hydrogen.

5. The compound as in claim 1, wherein X is $NR^7$; $R^1$, $R^2$, $R^3$, $R^4$, $R^5$ and $R^6$ are hydrogen, and $R^7$ is $C_1$–$C_6$ alkyl, carboxyl $C_1$–$C_6$ alkyl, phenyl $C_1$–$C_6$ alkyl, carboxyphenyl $C_1$–$C_6$ alkyl or amino $C_1$–$C_6$ alkyl.

6. The compound as in claim 1, wherein X is $NR^7$; $R^1$, $R^2$, $R^3$, $R^4$, $R^5$ and $R^6$ are hydrogen, and $R^7$ is isopropyl, carboxymethyl, benzyl, carboxybenzyl or aminopentyl.

7. A pharmaceutical composition comprising a pharmaceutically effective amount of a compound or a pharmaceutically acceptable salt thereof as claimed in claim 1, in admixture with a pharmaceutically acceptable carrier.

8. The compound as in claim 1, wherein X is oxygen.

9. The compound as in claim 1, wherein the compound is 2,4-bis(mercaptomethyl)-4-butanolide.

10. The compound as in claim 1, wherein the compound is 4-(1-mercapto-1-methylethyl)-2-mercaptomethyl-4-butanolide.

11. The compound as in claim 1, wherein the compound is 4-(1-mercapto-1-methylethyl)-4-mercaptomethyl-4-butanelactam.

12. The compound as in claim 1, wherein the compound is 2,4-bis(mercaptomethyl)-4-butanelactam.

13. A method of treating a patient suffering from an immunodeficiency disease or an autoimmune disease comprising administering to the patient a pharmaceutically effective amount of a compound, or a pharmaceutically acceptable salt thereof, according to claim 1, either alone or in admixture with a pharmaceutically acceptable carrier.

14. The method as in claim 13, wherein $R^1$ and $R^2$ are the same or different and each is hydrogen or methyl;

$R^3$ and $R^4$ are the same or different and each is hydrogen, methyl, carboxy or methoxycarbonyl;

$R^5$ and $R^6$ are the same or different and each is hydrogen, methyl, isopropyl, allyl, acetyl, pivaloyl, benzyl, methylbenzyl, methoxybenzyl, benzoyl, methylbenzoyl, methoxybenzoyl, trityl or tetrahydropyranyl;

$R^7$ is hydrogen, isopropyl, carboxymethyl, ethoxycarbonylmethyl, aminopentyl, dimethylaminopentyl, t-butoxycarbonylaminopentyl, benzylaminopentyl, methoxy, benzyl, methylbenzyl, methoxybenzyl, chlorobenzyl, carboxybenzyl, methoxycarbonylbenzyl, benzyloxy, methylbenzyloxy, methoxybenzyloxy or chlorobenzyloxy, and A is methylene, ethylene, trimethylene, tetramethylene, (dimethyl)methylene, (diethyl)methylene, (methyl)ethylene or (dimethyl)ethylene.

15. The method as in claim 13, wherein $R^1$, $R^2$, $R^3$, $R^4$, $R^5$ and $R^6$ are hydrogen, and X is oxygen.

16. The method as in claim 13, wherein the compound is selected from the group consisting of 2,4-bis(mercaptomethyl)-4-butanolide, 4-(1-mercapto-1-methylethyl)-2-mercaptomethyl-4-butanolide, 4-(1-mercapto-1-methylethyl)-2-mercaptomethyl-4-butanelactam and 2,4-bis(mercaptomethyl)-4-butanelactam.

17. The composition as in claim 7, wherein the compound is selected from the group consisting of 2,4-bis(mercaptomethyl)-4-butanolide, 4-(1-mercapto-1-methylethyl)-2-mercaptomethyl-4-butanolide, 4-(1-mercapto-1-methylethyl)-2-mercaptomethyl-4-butanelactam and 2,4-bis(mercaptomethyl)-4-butanelactam.

* * * * *